United States Patent
Roszell

(10) Patent No.: US 9,149,490 B2
(45) Date of Patent: Oct. 6, 2015

(54) ACNE TREATMENT COMPOSITION AND METHODS FOR USING

(75) Inventor: James A. Roszell, Las Vegas, NV (US)

(73) Assignee: Skinvisible Pharmaceuticals, Inc., Las Vegas, NV (US)

( * ) Notice: Subject to any disclaimer, the term of this patent is extended or adjusted under 35 U.S.C. 154(b) by 487 days.

(21) Appl. No.: 12/445,827

(22) PCT Filed: Oct. 19, 2007

(86) PCT No.: PCT/US2007/022299
§ 371 (c)(1),
(2), (4) Date: Sep. 22, 2010

(87) PCT Pub. No.: WO2008/051461
PCT Pub. Date: May 2, 2008

(65) Prior Publication Data
US 2011/0021447 A1     Jan. 27, 2011

Related U.S. Application Data

(60) Provisional application No. 60/853,074, filed on Oct. 20, 2006.

(51) Int. Cl.
*A61K 31/7056* (2006.01)
*A61K 31/60* (2006.01)
*A61P 17/10* (2006.01)
*A61K 31/7034* (2006.01)

(52) U.S. Cl.
CPC .................................. *A61K 31/7034* (2013.01)

(58) Field of Classification Search
USPC ............... 424/70.13, 70.15; 514/24, 161, 634
See application file for complete search history.

(56) References Cited

U.S. PATENT DOCUMENTS

| | | | |
|---|---|---|---|
| 4,126,699 A | 11/1978 | Gander et al. | |
| 4,139,625 A | 2/1979 | Sherlock | |
| 4,189,501 A | 2/1980 | Fulton, Jr. | |
| 5,312,834 A | 5/1994 | Yeo | |
| 6,117,843 A | 9/2000 | Baroody et al. | |
| 6,159,493 A | 12/2000 | Chen et al. | |
| 6,168,798 B1 | 1/2001 | O'Halloran et al. | |
| 6,433,024 B1 | 8/2002 | Popp et al. | |
| 7,008,647 B2 | 3/2006 | Burrell et al. | |
| 2003/0044436 A1* | 3/2003 | Roszell et al. ................. | 424/401 |
| 2004/0156873 A1* | 8/2004 | Gupta ........................... | 424/401 |
| 2005/0287097 A1 | 12/2005 | Roszell et al. | |
| 2006/0019935 A1* | 1/2006 | Watson ......................... | 514/171 |
| 2006/0128808 A1* | 6/2006 | Arsonnaud et al. ........... | 514/569 |

OTHER PUBLICATIONS

MedlinePlus Medical Dictionary. "Acne". 2011.*

* cited by examiner

*Primary Examiner* — Anna Falkowitz
(74) *Attorney, Agent, or Firm* — Merchant & Gould, P.C.

(57) ABSTRACT

An acne treatment composition is provided according to the present invention. The acne treatment composition includes an effective amount of an anti-acne component to provide anti-acne properties to skin tissue, an effective amount of a skin bounding polymer component to provide sustained release of the anti-acne component over a prolonged period of time after application of the acne treatment composition to skin tissue, and water. A method of using an acne treatment composition is provided.

21 Claims, 2 Drawing Sheets

ACNE TREATMENT COMPOSITION AND METHODS FOR USING

This application is being filed on 16 Apr. 2009, as a US National Stage of PCT International Patent application No. PCT/US2007/022299, filed 19 Oct. 2007 in the name of Skinvisible Pharmaceuticals, Inc., a U.S. national corporation, applicant for the designation of all countries except the US, and James A. Roszell, a citizen of the U.S., applicant for the designation of the US only, and claims priority to U.S. Provisional Patent Application Ser. No. 60/853,074, filed Oct. 20, 2006. To the extent appropriate, a claim of priority is made to each of the above disclosed applications.

FIELD OF THE INVENTION

The invention relates to an acne treatment composition and to methods for using an acne treatment composition. In particular, the acne treatment composition can include an effective amount of an anti-acne component, a skin bonding polymer component, and provides a sustained release the anti-acne component over a prolonged period of time.

BACKGROUND OF THE INVENTION

Aging, hormonal changes, and approaching adolescence often cause unsightly and embarrassing skin conditions which take the form of pimples, blemishes, pustules, and reddened areas. These skin problems take their toll not only in emotional anxiety and distress but also in physical marring of the skin, sometimes associated with pain, in both juveniles and adults. These skin problems can be referred to as acne, and can be exacerbated by environmental influences, such as, for example, improper diet, stress or tension, and lack of sleep.

Numerous compositions are available for treating acne. Many compositions are provided as wash or detergent compositions that are useful for cleaning skin tissue. Other compositions are intended to be applied and wiped off. Exemplary topical compositions are disclosed, for example, by U.S. Pat. No. 7,008,647 to Burrell et al., U.S. Pat. No. 6,433,024 to Popp et al., U.S. Pat. No. 6,159,493 to Chen et al., U.S. Pat. No. 6,117,843 to Baroody et al., U.S. Pat. No. 5,312,834 to Yeo, U.S. Pat. No. 4,189,501 to Fulton, Jr., U.S. Pat. No. 4,139,625 to Sherlock, U.S. Pat. No. 4,126,699 to Gander et al., and U.S. Pat. No. 6,168,798 to O'Halloran et al.

There is a desire to provide topical, acne treatment composition that provides a sustained release of an anti-acne active component over a prolonged period of time. Providing a sustained release of the anti-acne component over a prolonged period of time can provide for a continued application of the pharmaceutically active component, and can avoid tissue irritation that may result from application of a large dose of the anti-acne active component.

SUMMARY

An acne treatment composition is provided according to the present invention. The acne treatment composition includes an effective amount of an anti-acne component to provide anti-acne properties to skin tissue, an effective amount of a skin bounding polymer component to provide sustained release of the anti-acne component over a prolonged period of time after application of the acne treatment composition to skin tissue, and water.

A method for using an acne treatment composition is provided according to the present invention. The method includes a step of applying an acne treatment composition to skin tissue. The acne treatment composition includes an effective amount of an anti-acne component to provide anti-acne properties to the skin tissue, an effective amount of a skin bounding polymer component to provide sustained release of the anti-acne component over a prolonged period of time after application of the acne treatment composition to the skin tissue, and water.

A sustained release of the anti-acne component characterizes a release of the anti-acne component that is effective to provide anti-acne properties over the prolonged period of time. A prolonged period of time generally refers to a time period of at least about one hour. A prolonged time period can be a time of at least about two hours, or at least about four hours, if desired.

DETAILED DESCRIPTION

Figure 1:
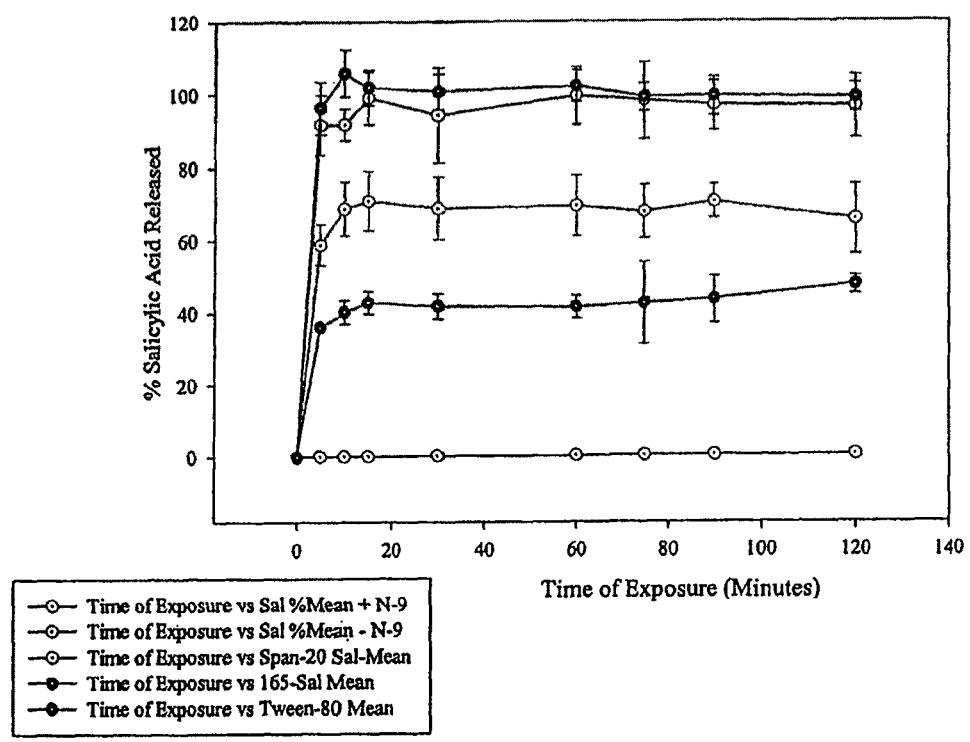
FIG. 1 is a graph showing the results of Example 1.

An acne treatment composition is provided that exhibits prolonged anti-acne properties. In general, anti-acne properties refer to antibacterial activity that treats the bacteria responsible for causing acne. Prolonged anti-acne properties refer to anti-acne properties that persist over a period of time. In general, the persistence can be considered sufficient so that the skin tissue having the acne treatment composition applied thereto delivers anti-acne properties for at least one hour after application of the composition to the skin tissue. The acne treatment composition preferably provides anti-acne properties at least about two hours after application to skin tissue, and more preferably provides anti-acne properties for at least about four hours after application to skin tissue.

The acne treatment composition can be applied to skin tissue on virtually any part of the body to provide anti-acne properties. Areas of the body often in need of anti-acne treatment include the face, the back, and the shoulders.

The acne treatment composition can be provided in the form of a lotion and applied to skin tissue by rubbing the composition onto the skin tissue. The acne treatment composition can have a viscosity that allows it to be applied to skin tissue conveniently as a lotion. The acne treatment composition can have a viscosity that is sufficiently high so that the lotion can be applied from a container (e.g., a tube or a bottle) to a person's hand or a location on the person's body, and the lotion can be rubbed onto the skin tissue. When provided as a lotion, the acne treatment composition can have a viscosity of greater than about 3,000 cSt (centistokes). The acne treatment composition can be provided in a form having a viscosity of less than about 3,000 cSt. When the acne treatment composition is provided having a viscosity of less than about 3,000 cSt, the acne treatment composition can be referred to as a liquid.

The acne treatment composition includes an anti-acne component, a skin bonding polymer component, and water. To provide a sustained release of the anti-acne component over a prolonged period of time, the acne treatment composition can contain a release agent. The release agent can be a surfactant. The acne treatment composition can be provided without a release agent if the composition provides a sustained release of the anti-acne component over a prolonged period of time without the presence of a release agent. Additional components that can be included in the skin disinfecting composition include pH modifying agent, coloring agent, preservative, thickening agent, emollient, humectant, antioxidant, fragrance, and chelating agent. The acne treatment composition can include any one or more of these additional components.

The acne treatment composition can be provided as an emulsion. Exemplary types of emulsions include oil in water emulsions, and water in oil in water emulsions.

Skin Bonding Polymer Component

The acne treatment composition can include a skin bonding polymer component. The skin bonding polymer component can include any polymer that, when applied to the skin, helps hold the anti-acne active component to the skin. The skin bonding polymer component holds the anti-acne active component to the skin tissue for a sufficient length of time to provide a desired treatment. The skin bonding polymer component can be referred to as the polymer component. The polymer component can be characterized as a polymer having an average molecular weight of at least about 2,000, and as a polymer having an average molecular weight of less than about 500,000.

The polymer component can include a hydrophobic polymer/hydrophilic polymer adduct and can include other components. Polymer components that can be used according to the invention include the topical compositions disclosed in U.S. Pat. No. 6,756,059. The entire disclosure of U.S. Pat. No. 6,756,059 is incorporated herein by reference.

The acne treatment composition can bind or adhere to skin tissue for a length of time, and can hold or contain the anti-acne component within the composition. It is expected that the acne treatment composition is able to adhere or bind to skin tissue for at least about one hour and preferably at least about two hours and hold the anti-acne component contained therein in proximity to skin tissue for that length of time. In general, it is expected that the acne treatment composition will adhere to skin tissue for a length of time sufficient to provide desired anti-acne properties.

The polymer component can be prepared from a topical composition precursor. The topical composition precursor can be prepared by melt processing a hydrophobic polymer composition and a hydrophilic polymer composition to provide an interaction between the hydrophobic polymer composition and the hydrophilic polymer composition. It should be understood that the phrase "melt processing" refers to mixing the hydrophobic polymer composition and the hydrophilic polymer composition under conditions that provide that the hydrophobic polymer component of the hydrophobic polymer composition and the hydrophilic polymer component of the hydrophilic polymer composition are in a liquid state so that they sufficiently mix. When the polymers are sufficiently mixed, it is believed that an interaction forms between the hydrophobic polymer component and the hydrophilic polymer component. The melt processing temperature can be at least about 50° C. and can be at least about 70° C. to generate this interaction.

It is believed the interaction exhibited between the hydrophobic polymer component and the hydrophilic polymer component is a type of complex formation reaction, and that the complex, once formed, can be stable in water at temperatures up to 65° C. and at a pH range of 3.0 to 9.0. By stable, it is meant that the complex does not favor disassociation under these conditions. It is believed that this interaction provides the acne treatment composition with an ability to bind or hold onto the anti-acne component that may be hydrophobic or relatively water insoluble, allows the acne treatment composition to be emulsified in water, and provides the acne treatment composition with an ability to bind to skin. The result of the interaction between the hydrophobic polymer component and the hydrophilic polymer component can be referred to as a hydrophobic polymer/hydrophilic polymer adduct. It should be understood that the term "adduct" is used to refer to the interaction between the hydrophobic polymer component and the hydrophilic polymer component. The interaction may be a form of complexing, but that is only theory. Accordingly, it should be understood that the term "adduct" is not meant to limit the polymer component to a particular theory of interaction.

It is believed that the interaction between the hydrophobic polymer component and the hydrophilic polymer component can be achieved more easily in the absence of water. It is expected that that if the hydrophilic polymer component becomes dissolved in water before forming the complex, it can be more difficult to sufficiently mix the hydrophobic polymer component and the hydrophilic polymer component to provide the desired level of interaction. Although a convenient technique for providing the desired level of interaction between the hydrophobic polymer component and the hydrophilic polymer component is melt mixing, it is expected that other techniques can be used to achieve the desired level of interaction. For example, it may be possible to use a nonaqueous solvent to help achieve the desired level of interaction.

The hydrophobic polymer composition that can be used according to the invention includes at least one hydrophobic polymer and can include a mixture of hydrophobic polymers. The hydrophobic polymer composition can include components having repeating pyrrolidone/alkylene groups. Exemplary polymers having repeating pyrrolidone/alkylene groups include poly(vinylpyrrolidone/alkylene) polymers. Poly(vinylpyrrolidone/alkylene) polymers include those polymers obtained by polymerizing alkylene substituted vinylpyrrolidone. Poly(vinylpyrrolidone/alkylene) polymers can be represented by the following general formula:

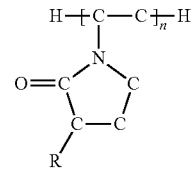

wherein R represents a carbon chain substitute such as an alkylene group and n represents the number of repeating units. The R group is preferably sufficiently long so that the polymer remains relatively water insoluble and should not be too long so that the polymer is difficult to melt process. The alkylene group can contain a length of at least about 10 carbon atoms and can contain less than about 30 carbon atoms. The alkylene group can contain about 14 carbon atoms to about 22 carbon atoms, and can contain about 15 carbon atoms to about 19 carbon atoms.

The poly(vinylpyrrolidone/alkylene) polymers that can be used according to the invention can have a molecular weight that is sufficiently high so that the polymer maintains its water insolubility but the molecular weight should not be so high that it becomes difficult to melt process the polymer. The weight average molecular weight of the poly(vinylpyrrolidone/alkylene) polymer can be between about 3,000 and about 400,000. Another way to characterize the size of the poly(vinylpyrrolidone/alkylene) polymer is by the number of repeating units (n). In the case of a poly(vinylpyrrolidone/alkylene) polymer having a weight average molecular weight of about 6,000 to about 30,000, the poly(vinylpyrrolidone/alkylene) polymer can have about 20 to about 80 repeating units, and can have about 30 to about 50 repeating units. It should be understood that repeating units refer to the residues of vinylpyrrolidone/alkylene groups.

Exemplary poly(vinylpyrrolidone/alkylene) polymers that can be used according to the invention include poly(vinylpyrrolidone/1-eicosene) and poly(vinylpyrrolidone/hexadecene). Poly(vinylpyrrolidone/1-eicosene) can be referred to as PVPE and is commonly used in pharmaceutical and cosmetic preparations. An exemplary form of PVPE for use according to the invention includes about 43 to 44 repeating units in length and has a weight average molecular weight of about 17,000 and can be characterized as a paraffin-like solid. This particular PVPE is highly insoluble in water, and has an extremely low oral toxicity ($LD_{50} > 17000$ mg/kg) and exhibits no demonstrable dermal toxicity. Poly(vinylpyrrolidone/1-hexadecene) can be referred to as PVPH. An exemplary form of PVPH is available as a viscous yellow liquid that is insoluble in water and has a low oral toxicity ($LD_{50} > 64000$ mg/kg), has about 39 to 40 repeating units, a molecular weight of about 14,000, and exhibits no demonstrable dermal toxicity.

PVPE and PVPH differ in the length of the hydrocarbon side chain, and are used extensively in the skin care industry, usually in concentrations of less than 1% by weight, because of their ability to bind to skin. Because the skin care industry generally prefers to apply actives to skin using a water-based composition, the use of PVPE and PVPH often requires solvents, surfactants, and emulsifiers to stabilize these polymers in a water emulsion. However, many of the solvents, surfactants and emulsifiers used to stabilize PVPE and PVPH in a water emulsion lack the low dermal toxicities of PVPE and PVPH. PVPE and PVPH by themselves lack a cosmetically elegant appeal when applied directly to the skin. They tend to be sticky and greasy.

The hydrophobic polymer composition used according to the invention can be provided as a mixture of different poly(vinylpyrrolidone/alkylene) polymers. The mixture of different poly(vinylpyrrolidone/alkylene) polymers can include at least 5 wt. % of a first poly(vinylpyrrolidone/alkylene) polymer based on the weight of the hydrophobic polymer composition. The hydrophobic polymer composition can include about 5 wt. % to about 54 wt. % of the first poly(vinylpyrrolidone/alkylene) polymer. The second poly(vinylpyrrolidone/alkylene) polymer can be provided in an amount of at least 46 wt. % and can be in a range of about 46 wt. % to 95 wt. % based on the weight of the hydrophobic polymer composition. For a hydrophobic polymer composition containing a first poly(vinylpyrrolidone/alkylene) polymer and a second poly(vinylpyrrolidone/alkylene) polymer, the mole ratio of the first polymer to the second polymer can be about 1:22 to about 1:1. When the hydrophobic polymer composition contains a mixture of different poly(vinylpyrrolidone/alkylene) polymers, the poly(vinylpyrrolidone/alkylene) polymers can be selected to provide improved properties compared to a composition having a hydrophobic polymer composition containing a single poly(vinylpyrrolidone/alkylene) polymer.

When the hydrophobic polymer composition is provided as a mixture of PVPH and PVPE, the PVPH can be provided in a range of about 46 wt. % to about 95 wt. % and the PVPE can be provided in a range of about 5 wt. % to about 65 wt. %, based upon the weight of the hydrophobic polymer composition.

The hydrophilic polymer composition that can be used according to the invention includes at least one hydrophilic polymer and may include a mixture of hydrophilic polymers. The hydrophilic polymers that can be used according to the invention include polymers having repeating carboxylic acid groups, hydroxyl groups, or both carboxylic acid groups and hydroxyl groups. Exemplary hydrophilic polymers that can be used according to the invention include polyacrylic acid polymers, poly(maleic acid/methylvinylether) copolymers, starch, derivatives of starch, polyvinyl alcohol, cellulose, derivatives of cellulous, carboxymethyl cellulous, cyclodextrins, dextrans, or mixtures thereof. The hydrophilic polymers should have a molecular weight that is not too high so that the hydrophilic polymer becomes difficult to process.

Polyacrylic acid polymers that can be used according to the invention include those having a weight average molecular weight of at least about 50,000. Polyacrylic acid polymers that can be used include those having a weight average molecular weight between about 50,000 to about 4,000,000. The polyacrylic acid polymers can have a level of cross-linking that is less than about 1% to help provide hydrophilic properties. A general structural representation of polyacrylic acid polymers is shown below:

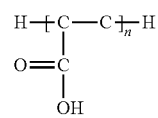

wherein n is the number of repeating units. The number n can be about 1,000 to about 20,000.

Poly(maleic acid/methylvinylether) copolymers that can be used according to the invention can have a weight average molecular weight of at least about 50,000, and can have a weight average molecular weight of about 50,000 to about 4,000,000. The weight average molecular weight can be about 70,000 to 2,500,000. A general structural representation of poly(maleic acid/methylvinylether) copolymers is shown below:

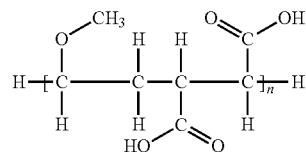

wherein n is the number of repeating units. The number n can be about 200 to about 20,000.

Additional hydrophilic polymers that can be used according to the invention include starch, derivatives of starch, polyvinyl alcohol, cellulose, derivatives of cellulose, carboxymethyl cellulose, cyclodextrins, and dextrans. The weight average molecular weight of the hydrophilic polymers is preferably sufficient to provide solubility in water but not too high to become difficult to process. Exemplary starches include amylopectin and polyglucose. Starches that can be used according to the invention can have a weight average molecular weight of about 50,000 to about 20,000,000. An exemplary starch component that can be used includes *Zea Mays* starch. A derivative of starch that can be used according to the invention includes partially hydrolyzed starch. Cellulose that can be used according to the invention can have a weight average molecular weight of about 50,000 to about 15,000,000. An exemplary cellulose component that can be used includes cellulose gum. Polyglucose that can be used according to the invention can be characterized as low fraction polyglucose having a weight average molecular weight of about 60,000 to about 90,000, and high fraction polyglucose having a weight average molecular weight of about 90,000 to about 300,000. An exemplary low fraction polyglucose material that can be used according to the invention is available under the name Dextran-70. In general, this type of polyglucose has all alpha 1-6 linkages. Starch derivatives that can be used according to the invention include those starch derivatives having alpha 1-4 linkages. An example of this type of starch derivative includes cyclodextrins. Exemplary cyclodextrins that can be used according to the invention include those that act to provide a cavity within the molecule large enough to contain components desirable for topical applications. Cyclodextrins that can be used according to the invention can have a molecular weight of about 900 to about 1,400. Polyvinyl alcohols that can be used according to the invention include those with a weight average molecular weight of about 50,000 to about 200,000.

Exemplary hydrophilic polymers that can be used according to the invention include those polymers having a melting temperature that allows for melt processing without decomposition of the polymer. Exemplary poly(maleic acid/methylvinylether) copolymers that can be used include those having a melting temperature range of about 60° C. to about 65° C. and a maximum temperature range of about 80° C. to about 90° C. The melting temperature refers to the temperature at which the polymer melts, and the maximum temperature refers to the temperature at which the polymer begins to decompose. Exemplary polyacrylic acid polymers that can be used include those having a melting temperature range of about 65° C. to about 70° C. and a maximum temperature range of about 80° C. to about 90° C. Exemplary carboxymethyl cellulose polymers that can be used include those having a melting temperature range of about 55° C. to about 60° C. and a maximum temperature range of about 75° C. to about 80° C. Exemplary polyvinyl alcohol polymers that can be used include those having a melting temperature range of about 50° C. to about 55° C. and a maximum temperature range of about 65° C. to about 70° C. Exemplary starches that can be used include those having a melting temperature range of about 40° C. to about 45° C. and a maximum temperature range of about 50° C. to about 55° C. Exemplary dextrans that can be used include those having a melting temperature range of about 37° C. to about 40° C. and a maximum temperature range of about 45° C. to about 50° C. Exemplary β-cyclodextrins that can be used according to the invention include those having a melting temperature range of about 40° C. to about 45° C. and a maximum temperature range of about 65° C. to about 70° C.

The hydrophobic polymer composition and the hydrophilic polymer composition can be combined and heated to at least about 50° C. to provide a polymer melt. The composition can be heated to at least about 70° C. under mixing to form complexes between the hydrophobic and hydrophilic polymers. It should be understood that a polymer melt refers to a polymer that flows or becomes a liquid when heated and is not meant to refer to a polymer that forms a liquid as a result of being dissolved in a solvent.

The complex formation step can be carried out in a relatively anhydrous environment. That is, the amount of water provided in the composition during the complex formation step can be less than about 1 wt. %. Once the desired level of complex formation has occurred, the composition can be hydrated with water.

The hydrophobic polymer composition and the hydrophilic polymer composition can be mixed together in amounts sufficient to provide a ratio of pyrrolidone groups to the combination of carboxylic acid groups and hydroxyl groups of about 1:1 to about 5:1. The ratio of the structures causing the observed interaction between the hydrophobic polymer composition and the hydrophilic polymer composition can be referred to as "functional group parity." The ratio of pyrrolidone groups to the combination of carboxylic acid groups and hydroxyl groups can be about 1.5:1 to about 3:1. In order to drive the complex formation reaction, it is desirable to provide an imbalance between the two types of groups. Accordingly, it is generally desirable to provide more of the pyrrolidone groups than the combination of carboxylic groups and the hydroxyl groups. It should be understood that the reference to a "combination of carboxylic groups and hydroxyl groups" refers to the total amount of carboxylic groups and hydroxyl groups present but does not require the presence of both carboxylic groups and hydroxyl groups. For example, the value of the combination of carboxylic groups and hydroxyl groups can be determined for a composition that contains only carboxylic groups. Similarly, the value can be determined for a composition that contains only hydroxyl groups.

During the complex formation step, the amounts of hydrophobic polymer composition and hydrophilic polymer composition can be characterized on a weight percent basis. For example, about 2 wt. % to about 28 wt. % hydrophilic polymer composition and about 72 wt. % to about 98 wt. % hydrophobic polymer composition can be combined to provide for complex formation. About 8 wt. % to about 25 wt. % hydrophilic polymer composition and about 72 wt. % to about 95 wt. % hydrophobic polymer composition can be combined to form the complex. During the complex formation step, the amount of water available in the composition can be less than about 1 wt. %. Although the complex forming composition can be relatively anhydrous, it is expected that the amount of water will be between about 0.3 wt. % and about 1.0 wt. %.

Once the hydrophobic polymers and the hydrophilic polymers have sufficiently reacted or interacted to form a complex, water can be added to the composition to provide a stable aqueous composition that can be relatively easily further hydrated. It has been found that the first hydration of the topical composition precursor is the most difficult hydration step because of the need to control the conditions of hydration. After the first hydration to a water content of at least about 30 wt. %, it is expected that further hydrations to higher water contents are relatively easy and can be accomplished by simply mixing the composition with water. Accordingly, the amount of water provided in the composition when made available as a concentrate for shipment is preferably between about 30 wt. % and about 45 wt. %. When the composition includes about 30 wt. % to about 45 wt. % water, it is expected that the composition can include about 3 wt. % to about 10 wt. % hydrophilic polymer composition and about 30 wt. % to about 50 wt. % hydrophobic polymer composition.

Water can be added to the relatively anhydrous composition by mixing water and the relatively anhydrous composition at a temperature and for a time sufficient to allow the composition to become hydrated without losing significant amounts of interaction between the hydrophobic polymer composition and the hydrophilic polymer composition. The relatively anhydrous composition can be hydrated by heating to at least 60° C. and adding water while mixing. The composition can be heated to at least about 65° C. and to at least about 70° C. An exemplary temperature range is about 65° C. to about 80° C.

The relatively anhydrous composition can be referred to as the topical composition precursor and generally refers to the hydrophobic polymer/hydrophilic polymer adduct. The polymer component for the hand disinfecting composition can refer to a composition that contains only the hydrophobic polymer/hydrophilic polymer adduct, and it can refer to a composition wherein the hydrophobic polymer/hydrophilic polymer adduct is diluted with water. In general, it is desirable to have a sufficient amount of water in the polymer component that allows one to formulate the polymer component into the skin disinfecting composition according to the invention. If there is too little water in the polymer component, it may become difficult to formulate the skin disinfecting composition. For example, the polymer component can contain water in an amount of up to about 95 wt. %. The polymer component can have a water concentration of about 30 wt. % to about 45 wt. %.

Additional components can be added to the skin bonding polymer component. For example, it may be desirable to add a component that helps stabilize the hydrophobic polymer/hydrophilic polymer adduct, and to help preserve and/or maintain the composition.

The skin bounding polymer component can advantageously assist in the treatment of acne by adsorbing skin oils which are thought to be a leading cause of acne.

The acne treatment composition can include the skin bonding polymer component in an amount sufficient to provide desired bonding properties of the composition. For example, the acne treatment composition can include about 3 wt. % to about 20 wt. % of the skin bonding polymer component, about 4 wt. % to about 15 wt. % of the skin bonding polymer component, or about 5 wt. % to about 8 wt. % of the skin bonding polymer component.

Anti-Acne Component

The acne treatment composition includes an anti-acne active component. The anti-acne active component can be referred to more conveniently as the anti-acne component. In general, the anti-acne component is a component that helps reduce or remove acne that is present or that helps prevent acne from forming or reduces the likelihood that acne will form. The anti-acne component, when provided so that it reduces or kills bacteria, it can be referred to as an antibiotic. Exemplary anti-acne active components include clindamycin, retinoic acid, salicylic acid, benzoyl peroxide, sulphacetamide, adapalene, or mixtures thereof.

Clindamycin that can be used includes a pharmaceutical grade salt or ester, usually being clindamycin phosphate. Clindamycin phosphate (ester) and clindamycin hydrochloride (salt) are exemplary forms of clindamycin. The preparation of suitable clindamycin and suitable lincomycin compounds are described in U.S. Pat. No. 3,969,516, the disclosure of which is incorporated herein by reference. Pharmaceutical grade clindamycin phosphate is available from commercial suppliers such as Genzyme Corporation, One Kendall Square, Cambridge, Mass. 02139.

Retinoic acid that can be used includes a pharmaceutical grade of retinoic acid. Exemplary forms of retinoic acid are disclosed in, for example, U.S. Pat. No. 3,729,568 and U.S. Pat. No. 4,126,699, the disclosure of which is incorporated herein by reference. Retinoic acid can be available under the name Tretinoin.

Benzoyl peroxide that can be used includes a pharmaceutical grade of benzoyl peroxide. Benzoyl peroxide may be in the form of a slurry of a finely divided powder, typically having a mean particle size of 35 µm, or lower, or in the form of a hydrous granular material. Preparation of suitable benzoyl peroxide constituents is well described in the medical and patent literature. See, for examples, the U.S. Pat. Nos. 3,535,422; 4,056,611; 4,387,107; and 4,923,900, the disclosures of which are incorporated herein by reference. Suitable benzoyl peroxide raw materials are available from commercial suppliers, such as the Norac Company, Azusa, Calif. An exemplary form of benzoyl peroxide includes dibenzoyl peroxide.

Salicylic acid and sulphatamide that can be used include pharmaceutical grades of salicylic acid and pharmaceutical grades of sulphacetamide.

Adapalene is considered a topical retinoid, and is available under the name Differin® from Galderma. Other topical retinoids can be used, if desired.

Various anti-acne components such as clindamycin and benzoyl peroxide can be considered relatively water soluble. As a result, clindamycin and benzoyl peroxide have a tendency to release from the acne treatment composition containing the skin bounding polymer component at a desired release rate over a prolonged period of time without the need for the presence of a release agent in the acne treatment composition. Although a release agent can be used to help assist with providing the desired level of release, it is possible to forgo the use of a release agent while still retaining a desired release rate when using relatively water soluble anti-acne components. In contrast, anti-acne components that are relatively water insoluble have a tendency to remain in the acne treatment composition. As a result, it can be desirable to include a release agent to help assist with the desired sustained release of a relatively water insoluble anti-acne component over a prolonged period of time.

Various amounts of the anti-acne component can be provided in the acne treatment composition. In general, the acne treatment composition can contain the anti-acne component in an amount of about 0.05 wt. % to about 12 wt. %. In general, retinoic acid can be provided at a level of about 0.05 wt. % to about 0.1 wt. %, clindamycin can be provided at a level of about 0.5 wt. % to about 1.5 wt. %, salicylic acid can be provided at a level of about 1.0 wt. % to about 3.0 wt. %, dibenzoyl peroxide can be provided at a level of about 5.0 wt. % to about 12.0 wt. %, and sulphacetamide can be provided at a level of about 3.0 wt. % to about 7.0 wt. %.

Water

The acne treatment composition can include water in an amount sufficient to allow the composition to be applied to skin tissue while providing the desired coverage over the skin tissue. The water component can be provided as deionized water, filtered water, distilled water, reverse osmosis water, or tap water. In the event that the water includes hardness or other components, it may be desirable to include builders, sequestrants, and chelating agents to handle the water hardness. In general, the acne treatment composition can include at least about 50 wt. % water. In addition, it is expected that if there is too much water, the emulsion might become unstable. In general, the amount of water in the acne treatment composition can be less than about 95 wt. %. The amount of water in the acne treatment composition can be about 65 wt. % to about 93 wt. %.

Release Agent

The acne treatment composition can include a release agent to assist with the sustained release of the anti-acne component over a prolonged period of time. The release agent can be provided as a surfactant. A surfactant can additionally be present to help maintain the acne treatment composition as an emulsion. In general, an emulsion refers to a composition that resists phase separation after sitting at room temperature for a couple of months. In general, it is expected that the acne treatment composition can be stored in a warehouse or in a storage closet for at least two months and can remain as an emulsion during that two month period. Preferably, the acne treatment composition can remain as an emulsion for at least one year or at least two years. The ability of the acne treatment composition to remain as an emulsion can be tested according to an accelerated stability test where the composition is held at 45° C. for two months. It is expected that this accelerated stability test for two months roughly corresponds to a period of about two years at room temperature. In general, it is expected that the hand disinfecting composition can remain as an emulsion after sitting for one month at 45° C. and preferably at least two months at 45° C.

Exemplary surfactants that can be used as the surfactant component include nonionic surfactants that help stabilize the emulsion and provide a generally even distribution of the anti-acne component. Exemplary nonionic surfactants that can be used include glycerol stearate such as glycerol monostearate, polysorbate such as that available under the name Tween 80, and polyoxyethylene stearate. In addition, mixtures of nonionic surfactants can be included including mixtures of polysorbate and glycerol stearate. An additional nonionic surfactant that can be used includes an ethoxy surfactant, a propoxy surfactant, or an ethoxy/propoxy surfactant. An exemplary ethoxy/propoxy surfactant includes a 10 carbon chain and 9 PO/EO surfactant available under the name Lutensol XP-90 from BASF. Additional nonionic surfactants include sorbitan monolaurate and sorbitan monostearate. Additional surfactants that can be used include those that are generally characterized as Pluronic surfactants such as poloxamers, and Lutensol surfactants such as $C_{10}$ polyoxyethylene.

It is believed that anionic surfactants may be useful as part of the surfactant component. In general, it is expected that anionic surfactants have a greater tendency to cause irritation to skin tissue.

The acne treatment composition can include an amount of surfactant component sufficient to provide the composition with a desired emulsion stability and sufficiently low viscosity without foaming. The amount of the surfactant component in the acne treatment composition, can be about 0.5 wt. % to about 6 wt. %, and can be about 1 wt. % to about 5 wt. %. It should be understood that the acne treatment composition can be provided without any surfactant component, if desired.

The acne treatment composition can contain a release agent to assist with the sustained release of the anti-acne component over a prolonged period of time. A sustained release of the anti-acne component refers to a release, over the time period, wherein the release provides anti-acne properties. In general, it is desirable for the acne treatment composition to provide a relatively consistent release of the anti-acne component after application of the acne treatment composition to skin tissue, and for a period up to at least one hour, preferably at least two hours, and preferably at least four hours. A relatively consistent release can be characterized as a release rate at one hour that is within about 50% of the release rate at 30 minutes. In addition, a relatively consistent release rate can be characterized as a release rate at two hours that is within about 50% of the release rate at 30 minutes. Preferably, these release rates can be provided within about 25%, and more preferably can be provided within about 15%.

At least two advantages can be obtained by providing a sustained release rate or a relatively constant release rate over a prolonged period of time. For example, by providing a sustained release of the anti-acne component over a prolonged period of time, it is possible to prolong the pharmaceutical activity of the acne treatment composition after application to skin tissue. By prolonging the pharmaceutical activity of the acne treatment composition, it is expected that enhanced performance in reducing acne or reducing the likelihood of acne occurring can be enhanced. Furthermore, by controlling the release of the anti-acne component so that it is not released at one instant in time, it is possible to reduce or minimize skin irritation. Many anti-acne components have a tendency to cause skin irritation if provided at a concentration that is too high. By controlling the release of the anti-acne component, it is possible to reduce the tendency of the anti-acne component to cause skin irritation because too much of it is released at one time.

pH Adjusting Agent

The acne treatment composition can include a pH adjusting agent or neutralizing agent to provide the acne treatment composition with a pH that helps stabilize the anti-acne component. Exemplary pH adjusting agents that can be used include sodium hydroxide, potassium hydroxide, triethanolamine, and mixtures thereof.

The polymer component of the lotion may be at least in part responsible for reducing the irritability of the acne treatment composition. For example, it is believed that the polymer component may help reduce irritation of skin tissue. The acne treatment composition can be provided without any pH modifier, if desired.

Thickener

Thickeners that can be incorporated into the acne treatment composition include those components that thicken or increase the viscosity of the acne treatment composition so that the acne treatment composition can be readily applied to skin. Thickeners that can be used in the acne treatment composition include those components often referred to as viscosity controlling agents.

Exemplary thickeners or viscosity controlling agents that can be provided in the hand disinfecting composition include cellulose gum, alkane triols; acrylates; substituted celluloses such as hydroxy ethyl cellulose, carboxymethyl cellulose, methylcellulose, and hydroxypropyl cellulose; cetyl alcohol; gums such as natural gums or synthetic gums; long chain alcohols such as those having about 9 to about 24 carbon atoms; polyglycols such as polyethylene glycols, polypropylene glycols, polybutylene glycols, polyethylene propylene glycols, or mixtures thereof; waxes such as natural waxes or synthetic waxes; hydrogenated oils; glycol esters; fatty acid esters; long chain acids; acid amides; silicates; and mixtures thereof. An exemplary thickener that can be used is hydroxyethyl cellulose.

The acne treatment composition may or may not include a thickener. When the acne treatment composition includes a thickener, the thickener can be provided in an amount that provides the desired level of thickening. The acne treatment composition can include a thickener in an amount of least about 0.1 wt. % and can include a thickener in an amount of at least about 0.4 wt. %. In addition, the thickener can be provided in an amount of less than about 2 wt. %, and can be provided in an amount of less than about 1.0 wt. %.

Emollient

The acne treatment composition can include an emollient for improving the texture of the composition. An emollient is an oleaginous or oily substance which helps to smooth and soften the skin, and may also reduce its roughness, cracking or irritation. Exemplary suitable emollients include mineral oil, having a viscosity in the range of 50 to 500 centipoise (cps), lanolin oil, coconut oil, cocoa butter, olive oil, almond oil, *macadamia* nut oil, synthetic jojoba oils, natural sonora jojoba oils, safflower oil, corn oil, liquid lanolin, aloe vera, cottonseed oil, and peanut oil.

Other suitable emollients include squalane, castor oil, polybutene, odorless mineral spirits, sweet almond oil, avocado oil, clophyllum oil, ricin oil, vitamin E acetate, olive oil, linolenic alcohol, coconut oil, oleyl alcohol, the oil of cereal germs such as the oil of wheat germ, isopropyl palmitate, octyl palmitate which is commercially available as Lexol EHP, tradename of Inolex Co. of Philadelphia, Pa., isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glycerol, ricin oleates of alcohols and poly alcohols such as those of isopropyl adipate, hexyl laurate and octyl dodecanoate.

Other suitable emollients which are solids or semi-solids at room or ambient temperatures may be used in amounts sufficient to provide liquid topical compositions. Such solid or semi-solid cosmetic emollients include hydrogenated lanolin, hydroxylated lanolin, acetylated lanolin, petrolatum, isopropyl lanolate, butyl myristate, cetyl myristate, myristyl myrislate, myristyl lactate, cetyl alcohol, isostearyl alcohol and isocetyl lanolate. Exemplary emollients include stearic acid, stearyl alcohol, palmitic acid enters natural and synthetic esters such as coconut oil.

The acne treatment composition can include the emollient in an amount sufficient to provide a silky feel. An exemplary range of the emollient in the acne treatment composition can be at least about 0.5 wt. %. In addition, the acne treatment composition can include an emollient in an amount of less than about 3 wt. %. It should be understood that the emollient is an optional component of the acne treatment composition. The acne treatment composition can be provided without an emollient, if desired.

Moisturizer

The acne treatment composition can include a moisturizer to provide a desired moisturizing effect to skin tissue. The moisturizer can be provided as a humectant. In general, a humectant is a moistening agent that promotes retention of water due to its hydroscopic properties. Exemplary humectants include glycerine, polymeric glycols such as polyethylene glycol and polypropylene glycol, and sorbitols such as sorbitol solution, pyrrolidone carboxylic acid, urea, or mixtures thereof. The acne treatment composition can be provided without a moisturizer.

When the acne treatment composition includes a moisturizer, it can be included in an amount of at least about 0.5 wt. %. In addition, the acne treatment composition can include a moisturizer in an amount of less than about 5 wt. %.

Preservatives

The acne treatment composition can include preservatives for prevention of bacterial, fungal, and/or yeast contamination. Exemplary preservatives that can be used in the hand disinfecting composition include phenoxyethanol, benzoic acid, derivatives and salts of benzoic acid, parabens, oxazolidines; chlorinated aromatic compounds and phenols, hydantoins, cresols and derivatives, imiazolindinyl urea, iodopropanol butylcarbamate, sulfites, and bisulfites. The acne treatment composition can include any of the preservatives commonly used or known to be suitable for topically applied compositions. Exemplary commercially available preservatives include liquid Germal Plus (diazolidinyl urea and iodopropynyl butylcarbamate) and Germaben 11 (diazolidinyl urea and methylparaben and propylparaben).

The acne treatment composition can be formulated without a preservative. It is expected that the preservative will increase the shelf life of the acne treatment composition by reducing or preventing the growth of bacteria, fungus, and/or yeast. When the acne treatment composition includes a preservative, the preservative is preferably provided in an amount sufficient to provide a desired level of protection from growth of bacteria, fungus, and/or yeast.

In general, for most preservatives, it is expected that the amount of preservative can be provided at a level of about 0.1 wt. % to about 1.0 wt. %, and can be provided at a level of about 0.2 wt. % to about 0.5 wt. %, based on the weight of the acne treatment composition.

Antioxidants

The acne treatment composition can include antioxidants to help increase the shelf life of the acne treatment composition and to provide desired properties when applied to skin tissue. Exemplary antioxidants that can be used include vitamins such as vitamin E, vitamin E acetate, vitamin C, vitamin A, and vitamin D, and derivatives thereof. Exemplary antioxidants include α-tocopherols which can be characterized as natural or synthetic Vitamin E. Additional exemplary antioxidants include propyl, octyl and dodecyl esters of gallic acid, butylated hydroxyanisole (BHA) (usually as a mixture of ortho and meta isomers), butylated hydroxytoluene (BHT), and nordihydroguaiaretic acid, and alkylated parabens such as methylparaben and propylparaben.

The acne treatment composition can be formulated without an antioxidant. When the acne treatment composition includes an antioxidant, the antioxidant can be provided in an amount that provides antioxidant properties in the acne treatment composition. In general, it is expect that the antioxidant can be provided in an amount of about 0.2 wt. % to about 2 wt. %, and can be provided in an amount of about 0.7 wt. % to about 1.5 wt. %, based on the weight of the acne treatment composition. In the case of vitamin E, it is expected that the vitamin E can be included in the acne treatment composition in an amount of about 0.1 wt. % to about 1 wt. %, and can be included in an amount of about 0.3 wt. % to about 0.8 wt. %.

Chelating Agents

Chelating agents are substances used to chelate or bind metallic ions with a certain heterocyclic ring structure so that the ion is held by chemical bonds from each of the participating rings. Suitable chelating agents include ethylene diaminetetraacetic acid (EDTA), EDTA trisodium, EDTA tetrasodium, calcium disodium edetate, EDTA trisodium, EDTA tetrasodium and EDTA dipotassium. One or more chelating agents can optionally be included in the emulsion in amounts ranging from about 0.001 to about 0.1 weight percent. It should be appreciated that the acne treatment composition can be provided without a chelating agent.

Fragrances

Fragrances are aromatic compounds which can impart an aesthetically pleasing aroma to the acne treatment composition. Typical fragrances include aromatic materials extracted from botanical sources (i.e. rose petals, gardenia blossoms, jasmine flowers, etc.) which can be used alone or in any combination to create essential oils. Alternatively, alcoholic extracts may be prepared for compounding fragrances. One or more fragrances can optionally be included in the composition in an amount ranging from about 0.001 to about 10 weight percent, preferably about 0.05 to about 5 percent. It should be appreciated that the acne treatment composition can be provided without a fragrance.

Carriers, Diluents, and Excipients

The acne treatment composition may also include nontoxic, pharmaceutically and dermatologically acceptable carriers, diluents and excipients, suitable for topical application, as are well known, see for example Merck Index, Merck & Co., Rahway, N.J., Bioreversible Carriers in Drug Design, Theory and Application, Roche (ed.) Pergamon Press, (1987), Gilman et al., (eds) (1990) Goodman and Gilman's: The Pharmacological Bases of Therapeutics, 8th Ed., Pergamon Press, Novel Drug Delivery Systems, 2nd Ed., Norris (ed.) Marcel Dekker Inc., (1989), and Remington's Pharmaceutical Sciences. For standard dosages of conventional pharmacological agents, see, e.g., Physicians Desk Reference (1997 Edition); and American Medical Association (1997) Drug Evaluations (Subscriptions).

An exemplary acne treatment composition can be provided according to Table 1.

TABLE 1

Acne Treatment Composition

| Component | Amount (wt. %) |
| --- | --- |
| Skin binding polymer component | 3-20 |
| Anti-acne active component | 0.05-.2 |
| Release agent | 0.5-6 |
| Thickener | 0.1-2 |
| Emollient | 0.5-3 |
| Humectant | 0.5-5 |
| Preservative | 0.1-1 |
| Water | balance |

Example 1

Exemplary acne treatment compositions were evaluated for the release of salicylic acid over time. The base composition includes 8 wt. % skin bonding polymer component based on starch and poly(vinylpyrrolidone/alkylene), 2 wt. % salicylic acid, 0.5 wt. % thickener (CM cellulose), 1 or 2 wt. % surfactant, and the balance water. The tested composition contained 2 wt. % Span-20 (sorbitan monolaurate), 1 wt. % Arlacel 165 (polyoxyethylene stearate and glycerol monostearate), 1 wt. % Tween-80 (polysorbate), and 1 wt. % Nonoxynol-9.

The percent salicylic acid released was measured as a function of time. The results are shown in FIG. 1. In FIG. 1, the bottom line represents the base composition containing no surfactant, the next line up represents the composition containing arlacel 165 surfactant, the next line up represents the composition containing span-20 surfactant, and the next two lines represent the compositions containing Tween-80 and Nonoxynol-9.

Example 2

Figure 2:
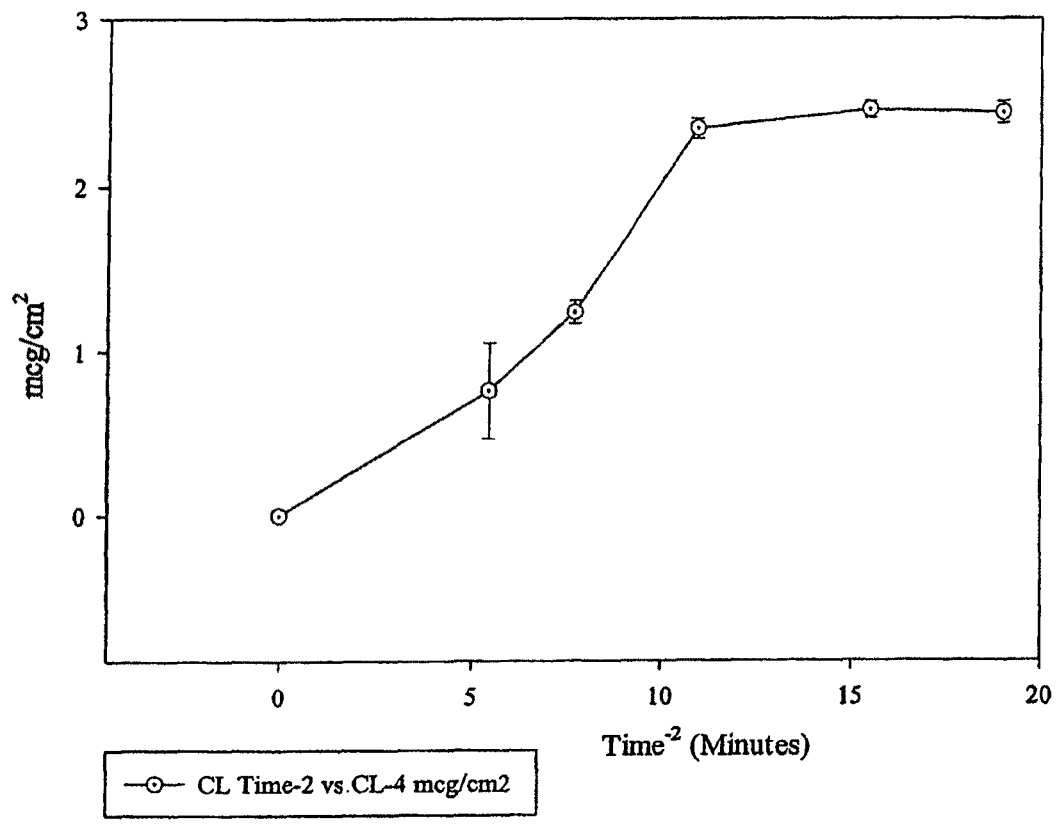
FIG. 2 is a graph showing the results of Example 2.

This example was conducted to determine the rate of clindamycin release over time. The composition tested included about 8 wt. % skin bonding polymer component based on cellulose gum and poly(vinylpyrrolidone/alkylene), 1 wt. % clindamycin, and the balance water. The results of this example are reported in FIG. 2. This example shows a sustained release of high levels of clindamycin for four hours.

I claim:

1. An acne treatment composition comprising:
   (a) about 0.05 wt. % to about 0.2 wt. % adapalene;
   (b) an effective amount of a skin bonding polymer component to provide sustained release of the adapalene over a prolonged period of time after application of the acne treatment composition to skin tissue, wherein the skin bonding polymer component comprises a hydrophobic polymer/hydrophilic polymer adduct wherein the hydrophobic polymer comprises poly(vinylpyrrolidone-alkylene) polymer wherein the alkylene group contains about 10 carbon atoms to about 30 carbon atoms, and the hydrophilic polymer comprises cellulose;
   (c) about 0.5 wt. % to about 6 wt. % of a surfactant; and
   (d) water,
   wherein the composition provides a sustained release of the adapalene for at least two hours after application of the composition to skin tissue.

2. The acne treatment composition according to claim 1, wherein the composition provides a release of the adapalene, after application to skin tissue, wherein the release rate at one hour is within about 50% of the release rate at 30 minutes.

3. The acne treatment composition according to claim 1, wherein the composition comprises at least about 50 wt. % water.

4. The acne treatment composition according to claim 1, wherein the composition comprises about 0.1 wt. % to about 2 wt. % of a thickener.

5. The acne treatment composition according to claim 1, wherein the composition comprises about 0.5 wt. % to about 5 wt. % of a moisturizer.

6. The method for using an acne treatment composition comprising:
   applying the acne treatment composition to skin tissue, wherein the acne treatment composition comprises:
   (a) about 0.05 wt. % to about 0.2 wt. % adapalene;
   (b) an effective amount of a skin bonding polymer component to provide sustained release of the adapalene over a prolonged period of time after application of the acne treatment composition to the skin tissue, wherein the skin bonding polymer component comprises a hydrophobic polymer/hydrophilic polymer adduct wherein the hydrophobic polymer comprises poly(vinylpyrrolidone-alkylene) polymer wherein the alkylene group contains about 10 carbon atoms to about 30 carbon atoms, and the hydrophilic polymer comprises cellulose;
   (c) about 0.5 wt. % to about 6 wt. % of a surfactant; and
   (d) water
   wherein the composition provides a sustained release of the adapalene for at least two hours after application to skin tissue.

7. The method according to claim 6, wherein the skin tissue comprises skin tissue provided on a person's face.

8. The method according to claim 6, wherein the composition provides a release of the adapalene, after application to skin tissue, wherein the release rate at one hour is within about 50% of the release rate at 30 minutes.

9. The method according to claim 6, wherein the composition comprises at least about 50 wt. % water.

10. The method according to claim 6, wherein the composition comprises about 0.1 wt. % to about 2 wt. % of a thickener.

11. The method according to claim 6, wherein the composition comprises about 0.5 wt. % to about 5 wt. % of a moisturizer.

12. The method according to claim 6, wherein the cellulose has a weight average molecular weight of about 50,000 to about 15,000,000.

13. The method according to claim 6, wherein the cellulose comprises carboxymethyl cellulose.

14. The method according to claim 6, wherein the hydrophobic polymer/hydrophilic polymer adduct comprises about 2 wt. % to about 28 wt. % of the hydrophilic polymer and about 72 wt. % to about 98 wt. % of the hydrophobic polymer.

15. The acne treatment composition according to claim 1, wherein the cellulose has a weight average molecular weight of about 50,000 to about 15,000,000.

16. The acne treatment composition according to claim 1, wherein the cellulose comprises carboxymethyl cellulose.

17. The acne treatment composition according to claim 1, wherein the hydrophobic polymer/hydrophilic polymer adduct comprises about 2 wt. % to about 28 wt. % of the hydrophilic polymer and about 72 wt. % to about 98 wt. % of the hydrophobic polymer.

18. The acne treatment composition according to claim 1, wherein the composition provides a sustained release of the adapalene for at least four hours after application of the composition to skin tissue.

19. The method according to claim 6, wherein the composition provides a sustained release of the adapalene for at least four hours after application of the composition to skin tissue.

20. The acne treatment composition according to claim 1, wherein the composition comprises about 0.1 wt. % to about 1.0 wt. % of an antioxidant comprising Vitamin E, Vitamin E acetate, Vitamin C, Vitamin A, or Vitamin D.

21. The method according to claim 6, wherein the composition comprises about 0.1 wt. % to about 1.0 wt. % of an antioxidant comprising Vitamin E, Vitamin E acetate, Vitamin C, Vitamin A, or Vitamin D.

\* \* \* \* \*